United States Patent
Henderson et al.

(10) Patent No.: US 10,194,888 B2
(45) Date of Patent: Feb. 5, 2019

(54) CONTINUOUSLY ORIENTED ENHANCED ULTRASOUND IMAGING OF A SUB-VOLUME

(71) Applicant: Siemens Medical Solutions USA, Inc., Malvern, PA (US)

(72) Inventors: Stephen Henderson, Menlo Park, CA (US); Tommaso Mansi, Plainsboro, NJ (US); Anand Tatpati, Sunnyvale, CA (US); Ingmar Voigt, Erlangen (DE); Bimba Rao, San Jose, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 826 days.

(21) Appl. No.: 14/656,159

(22) Filed: Mar. 12, 2015

(65) Prior Publication Data
US 2016/0262720 A1    Sep. 15, 2016

(51) Int. Cl.
*A61B 8/00* (2006.01)
*A61B 8/08* (2006.01)

(52) U.S. Cl.
CPC .............. *A61B 8/466* (2013.01); *A61B 8/469* (2013.01); *A61B 8/483* (2013.01); *A61B 8/5246* (2013.01); *A61B 8/085* (2013.01)

(58) Field of Classification Search
None
See application file for complete search history.

(56) References Cited

U.S. PATENT DOCUMENTS

| | | | |
|---|---|---|---|
| 5,873,830 A | 2/1999 | Hossack et al. | |
| 6,123,670 A | 9/2000 | Mo | |
| 8,945,012 B2 | 2/2015 | Ogasawara et al. | |
| 2005/0228280 A1* | 10/2005 | Ustuner | A61B 8/06 600/443 |
| 2007/0078342 A1* | 4/2007 | Jago | A61B 8/00 600/443 |
| 2007/0078344 A1* | 4/2007 | Rafter | A61B 8/08 600/450 |
| 2009/0310837 A1 | 12/2009 | Park et al. | |
| 2011/0144495 A1* | 6/2011 | Wilkening | A61B 8/0883 600/443 |
| 2012/0232379 A1 | 9/2012 | Ionasec et al. | |

FOREIGN PATENT DOCUMENTS

JP    2007029335    2/2007

\* cited by examiner

Primary Examiner — Katherine Fernandez

(57) ABSTRACT

An entire volume is scanned. A sub-volume is separately scanned with different settings for beamforming parameters, allowing greater image quality for the sub-volume while providing context from the volume. The anatomy of interest is periodically detected, and the sub-volume shifted in position to cover the anatomy of interest, allowing for relatively continuous volume imaging with enhanced quality imaging of the sub-volume. Interleaving by volume and sub-volume slices may allow for optimization of relative frame rate and image quality. Different combinations between volume and sub-volume data for anatomy detection and display may provide for desired imaging while allowing the regular detection of the anatomy.

11 Claims, 4 Drawing Sheets

US 10,194,888 B2

CONTINUOUSLY ORIENTED ENHANCED ULTRASOUND IMAGING OF A SUB-VOLUME

BACKGROUND

The present embodiments relate to volume imaging in ultrasound. In particular, volume imaging with a region of interest is provided.

In ultrasound imaging, there are well-known trade-offs between frame-rate, resolution, penetration, and contrast. For example, acquisition of real-time volume images with a reasonable field-of-view and at a rate acceptable for cardiology inevitably involves significant sacrifice of image quality (e.g., resolution and/or contrast) relative to the best possible quality achieved at a lower rate. In some cases, it will be desirable or necessary to maintain a full field of view of larger anatomy, such as the heart, when a particular part of anatomy within the heart, such as a valve, is of prime interest. This results in a lesser quality view of the anatomy of particular interest.

To improve image quality of a particular part of the anatomy, the user manually repositions a region of interest around the targeted feature, decreases the size of the region being scanned to only encompass the delimited region-of-interest, and then further adjusts imaging parameters to enhance the image quality. Such a process is cumbersome. The process also requires expertise and attention on the part of the user, especially in a volume imaging context. The process further results in a loss of context due to the reduced field of view.

The reduced field of view is prone to failure due to probe movement relative to the anatomy. Either the probe or anatomy may move and cause the feature of interest to move out the smaller volume and be lost. The likelihood of this outcome is only reduced by making the region of interest conservatively larger than the anatomy of interest to keep the field of view over some full possible range of motion. But the field of view increase in size necessarily comes through a sacrifice of frame-rate and/or image quality within the smaller volume.

BRIEF SUMMARY

By way of introduction, the preferred embodiments described below include methods and systems for enhanced ultrasound imaging of a sub-volume. An entire volume is scanned. A sub-volume is separately scanned with different settings for beamforming parameters, allowing greater image quality for the sub-volume while providing context from the volume. The anatomy of interest is periodically detected, and the sub-volume shifted in position to cover the anatomy of interest, allowing for relatively continuous volume imaging with enhanced quality imaging of the sub-volume. Interleaving by volume and sub-volume slices may allow for fine-grained optimization of relative frame rate and image quality. Different combinations between volume and sub-volume data for anatomy detection and display may provide for desired imaging while allowing the regular detection of the anatomy. Any one or more of these features may be used independently or in combination.

In a first aspect, a method of enhanced ultrasound imaging of a sub-volume is provided. An ultrasound imaging system scans a volume of a patient with different values for scan settings for the sub-volume of the volume than for other parts of the volume. A processor tracks a position within the volume of anatomy. The tracking uses data resulting from the scanning. The processor alters a location of the sub-volume within the volume based on the tracking so that the anatomy is in the sub-volume. The scanning is repeated with the altered location. First and second images are generated in sequence from the data of the scanning and repetition of the scanning, respectively.

In a second aspect, a system is provided for enhanced ultrasound imaging of a sub-volume. A transducer is connectable with the transmit and receive beamformers. A beamformer controller is configured to cause the transmit and receive beamformers to: scan a volume of a patient, the volume including a plurality of volume regions sequentially scanned during the scan of the volume; scan a sub-volume of the volume, the sub-volume including a plurality of sub-volume regions sequentially scanned during the scan of the sub-volume; and interleave the scan of the volume regions with the scan of the sub-volume regions so that at least one of the volume regions is scanned before scanning all of the sub-volume regions and at least one of the sub-volume regions is scanned before scanning all of the volume regions. An image processor is configured to generate an image of the patient using data from the scan of the volume and data from the scan of the sub-volume. A display is configured to display the image.

In a third aspect, a method of enhanced ultrasound imaging of a sub-volume is provided. A volume is scanned. A sub-volume of the volume is scanned with a greater frame rate, resolution, contrast, or combinations thereof. Data from the scanning of the volume is combined with data from the scanning of the sub-volume. A measurement is performed from the combined data. The data from the scanning of the volume and the data from the scanning of the sub-volume are passed to a three-dimensional renderer. The three-dimensional renderer generates an image where the data of the main volume is rendered differently than the data of the sub-volume.

The present invention is defined by the following claims, and nothing in this section should be taken as limitations on those claims. Further aspects and advantages of the invention are disclosed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Automated, continuously oriented enhanced imaging of a sub-volume is provided. Enhanced image quality of a targeted part of the anatomy is provided in a way still compatible with imaging of the larger region around the anatomy. While providing enhanced sub-volume imaging in combination with full volume imaging, a practical and largely transparent workflow results. The user merely configures the system for volume imaging for a particular anatomy, and the imaging system provides both context (e.g., full volume) and high quality information (e.g., sub-volume) to the end user. A combination of automated continuous anatomical detection with the enhanced live volume imaging is provided. There is little or no disruption from a normal user experience or measurement workflow, other than improved imaging of the anatomy.

The sub-volume is continuously oriented around an automatically detected anatomical feature during live scanning, with enhanced scanning in the sub-volume to achieve superior imaging of the feature. Orientation of the sub-volume is an automatic background process by being preset driven and not requiring extra user interactions. The detection of the movement of anatomy may be used to predict the future location of anatomy for setting the sub-volume location during live scanning.

The volume and sub-volume scanning may be interleaved slice-by-slice, allowing more refined trade-off of frame rate with image quality than by interleaving full volume scan with full sub-volume scan. Interleaving of sub-volume and main-volume scanning may be performed on the basis of azimuth sweeps. A range of non-integer relative volume rates may be provided between the sub-volume and main volume, with temporal coherence maximized in each sweep to support lateral analytic processing.

Since the desired information used for anatomy detection or other measurements may be different than for live imaging, multiple data paths may be used. The sub-volume and volume data are blended for measurements, but remain separated until rendering for imaging. For example, one path blends pre-CINE for consumption by measurements, another path blends post-cine for display enhancements of the sub-volume seen by user.

Figure 1:
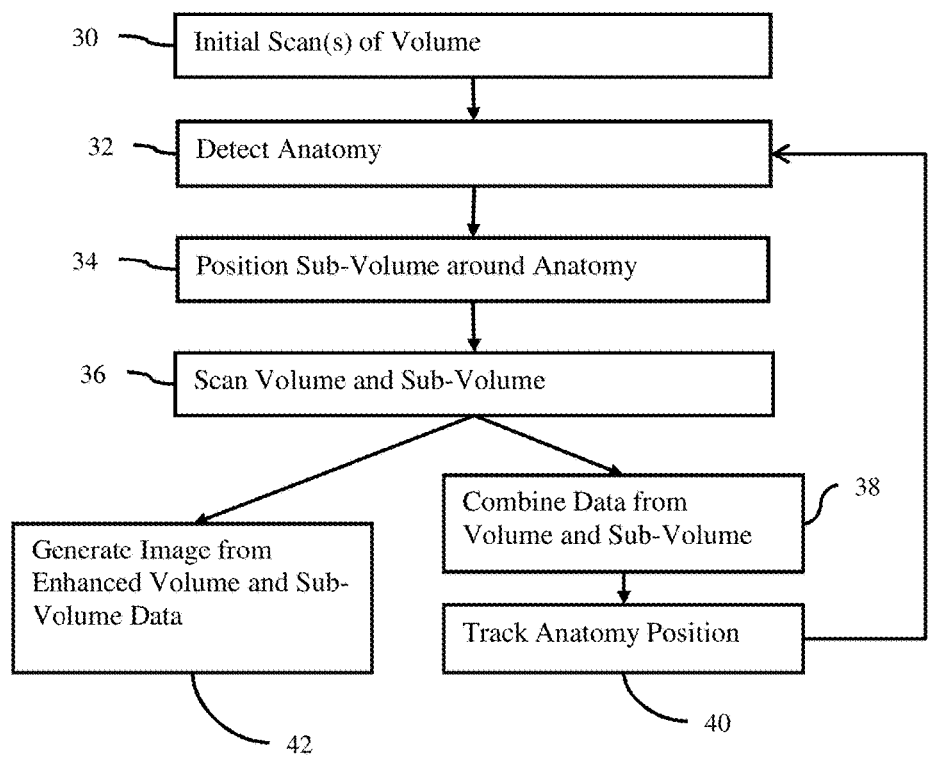
FIG. 1 is a flow chart diagram of one embodiment of a method for enhanced ultrasound imaging of a sub-volume.

FIG. 1 shows one embodiment of a method of enhanced ultrasound imaging of a sub-volume. In general, anatomy of interest during three-dimensional ultrasound imaging is detected automatically from a volume scan. A region of interest is defined as a sub-volume around the detected anatomy. The sub-volume is scanned interleaved with scans of the volume, providing sub-volume information with different scan settings than the rest of the volume. By repeating the detection of the anatomy with repetitions of the scanning, the anatomy location is updated, providing automatic volume imaging with enhanced imaging oriented at the anatomy of interest.

Figure 5:
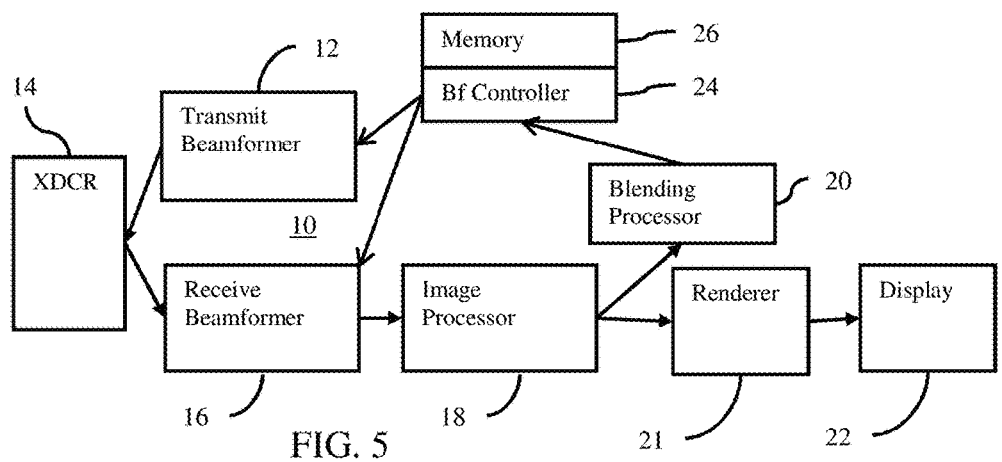
FIG. 5 is a block diagram of one embodiment of a system for enhanced ultrasound imaging of a sub-volume.

The method is performed by the system shown in FIG. 5 or a different system. For example, a medical diagnostic ultrasound imaging system scans in acts 30 and 36, a processor detects in acts 32 and 40, a beamformer controller positions the sub-volume within the volume in act 34, the processor combines data in act 38, and the imaging system generates the displayed image in act 42. Other devices may perform any of the acts, such as the processor performing all of the non-scan acts.

The acts are performed in the order shown or another order. For example, act 42 is performed before, after, or simultaneously with acts 38 and 40 and/or repetition of acts 34 or 36.

Additional, different or fewer acts may be used. For example, act 42 may not be performed. As another example, act 38 may not be performed and the anatomy is detected using volume data without combination with sub-volume data. In yet another example, the repetition loop from act 40 to act 32 and the tracking of act 40 are not performed, such as where acts 38 and 42 are performed with combined and uncombined data in two paths for a single image.

In act 30, a volume of a patient is scanned. This scan is an initial scan, such as a first scan. The initial scan may be the one occurring initially or before anatomy is detected in act 32, even if other previous scans occur before the initial scan.

The initial scan is of an entire volume. The entire volume is a field of view established by the scanning. The lateral extent and depth define the extent of the scanned volume. Based on different settings, different size volumes may make up the entire scan volume. The user or the system determines the field of view and resulting entire scan volume.

To scan a field of view with ultrasound, transmit and receive beams are formed by an ultrasound system. Any scan format, such as sector, linear, or Vector®, and corresponding field of view may be used. The scanning is of a three-dimensional region or a volume. The scan lines are distributed by electric and/or mechanical steering in three-dimensions, providing data representing a volume (e.g., volume of N×M×R, where N, M, and R are integers greater than 1). Any three-dimensional format may be used, such as scanning sequentially along planes such that the scan planes together represent the volume.

The transmit and/or receive beam characteristics may be set or responsive to values of parameters. The depth and/or lateral extent of the field of view is set. Similarly, the transmit beam focal depth, transmit frequency, receive frequency, line density, sampling density, transmit waveform (e.g., number of cycles and/or envelope shape), frame rate, aperture, and/or other scanning characteristics are set. The number of transmit focal positions per scan line (e.g., one or two) may be set. Different, additional, or fewer scan (e.g., transmit and/or receive) parameters may be used.

Through receive beamformation, the responsive data represents samples in the field of view. Data received from the scanning is detected. A B-mode detector determines the intensity of acoustic echoes represented by the received data. For example, the receive data is formatted as in-phase and quadrature data. A square root of a sum of the squares of the in-phase and quadrature terms is calculated as the intensity. Other measures of the magnitude of the acoustic echo may be used for B-mode detection.

Other B-mode processing may be performed based on values for parameters. For example, the detected B-mode data is spatially filtered. As another example, a sequence of frames from a corresponding sequence of scans of the entire field of view is acquired. Different pairs or other sized groupings of the resulting B-mode frames of data are temporally filtered. Infinite impulse or finite impulse response filtering may be used. In another example, a general or overall gain is applied. One or more parameters may establish the overall gain. Additionally or alternatively, depth dependent gains may be applied. Different, additional, or fewer B-mode processing parameters may be used.

In other embodiments, other types of detection and corresponding scans are performed. For example, color flow (e.g., Doppler) estimation is used. Velocity, power, and/or variance are estimated. As another example, harmonic mode is used, such as imaging at a second harmonic of a fundamental transmit frequency. Combinations of modes may be used.

After processing, the detected data is scan converted, if needed. A two-dimensional image may be generated. For example, a B-mode image represents the intensity or strength of return of acoustic echoes in the B-mode field of view. The intensities or B-mode data is mapped to gray scale within the dynamic range of the display. The gray scale may be equal or similar red, green, blue (RGB) values used by the display to control pixels. Any color or gray scale mapping may be used.

Data used for other acts is from any point in the processing path. In one embodiment, detected and scan converted scalar values are used prior to any color or display mapping. In other embodiments, beamformed samples prior to detection, detected data before scan conversion, or display values after display mapping are used.

The values of the parameters for scanning are initially set using any process. In one embodiment, one or more of the parameters are set based on input by the user, predetermined values, and/or selection of an application or configuration. For example, the user selects volume or three-dimensional imaging of a particular anatomy, such as a heart valve. In alternative or additional embodiments, one or more of the parameters are set based on feedback or adapting to the data received from the scanning. Automatic setting of the value or values of the parameter or parameters is performed. For example, the overall gain and/or dynamic range of B-mode data is set based on identifying B-mode data for locations associated with tissue in the field of view and using an average, median or other B-mode intensity for the tissue locations to set the gain and/or dynamic range.

The values of the parameters may also be initially set for desired imaging quality enhancements. The values for the sub-volume to be separately scanned are set through presets. Multiple types of anatomy and image enhancements may be selected for different exam types. The user selects the volume imaging application for specific anatomy. The values for the scan settings for the volume and for the sub-volume are pre-determined and used based on the selection of the application. The user may alter or change any of the values for the volume and/or sub-volume scan.

In additional or alternative embodiments, one or more of the parameters may be set based on user input or adjustment. For example, the user selects a frequency or frame rate and/or line density using a multi-hz/space time selection or other input. As another example, the user selects a relative frame-rate between the main-volume (e.g., entire volume) and the sub-volume. In another example, the user inputs a minimum desired frame rate of the sub-volume). In yet another example, a relative weight of the main volume and the sub-volume is input for power management trade-offs. The user indicates the relative thermal burden, which then establishes frame rate and/or transmit power settings for the volume and sub-volume. Alternatively, values for one or more of these relative settings are established using presets or user selection of an application.

During live or real-time imaging (scanning and outputting images at the same time or while the patient has a transducer placed against them), no special interaction is generally required or expected of the user for the targeted sub-volume. The user may select only an application (e.g., three-dimensional imaging of a valve) and the remaining configuration automatically occurs. The user may pre-configure any one or more of the settings and then the imaging occurs without further change by the user. In other embodiments, configurability of the sub-volume and/or volume imaging is still available during the live imaging. The user may alter one or more values of scan parameters without being required or expected to alter as part of the normal workflow.

In act 32, a processor detects anatomy from the data of the initial scan. The data representing the volume of the patient is processed to detect the anatomy of interest. For example, the user translates and/or rotates the field of view (i.e., moves the transducer) relative to the patient to locate the anatomy. Once the anatomy is in the field of view, the processor detects the anatomy. For example, a valve is automatically detected from B-mode data representing a volume including at least a portion of a heart.

The detection is automatic during the live imaging. Rather than requiring user input of a location or locations for the anatomy, the processor applies filtering, edge detection, pattern matching, model matching, or other computer assisted classification to detect the anatomy in the data. In one embodiment, a machine-learnt classifier is applied. Haar, gradient, directional, or other features are calculated from the volume data and input to the machine-learnt classifier. The machine-learnt classifier, based on learning from training data with known truth distinguishing anatomy of interest from other tissue or fluid, indicates whether the anatomy is represented by the data for the volume and where. Any machine learning may be used, such as a probabilistic boosting tree, Bayesian network, neural network, or support vector machine. Any feature or feature set may be used.

In alternative embodiments, devices, such as surgical instruments or implants, are detected instead of anatomy. Anatomy and added devices may both be detected in a given volume. Different or the same detector detects the different anatomy and/or devices.

In yet other embodiments, the user manually identifies an arbitrary anatomical feature in the larger volume. The user inputs the location (e.g., tracing) of the anatomy. Semi-automated approaches may be used, such as the user inputting a seed point, which is then used to locate the anatomy.

The detected anatomy or device has any spatial extent. For example, the anatomy extends by multiple voxels in one or more dimensions.

In act 34, the processor assigns a sub-volume around or based on the detected anatomy. Where the detected anatomy is the anatomy of interest, the sub-volume is positioned to encompass the anatomy of interest with a minimum margin, such as 0.5 cm. When detected, the processor defines a sub-volume around the feature or anatomy. The sub-volume has any shape, such as a cube, sphere, or other shape. The sub-volume is sized to meet the margin while including all of the anatomy of interest. The sub-volume may be sized and shaped as the anatomy of interest with no or a given margin. In other embodiments, the sub-volume is positioned based on anatomy other than the anatomy of interest, such as positioning the sub-volume for a valve based on detection of a left ventricle.

The sub-volume extends over three dimensions. The sub-volume is within the volume, such as being entirely within or being within but having a common edge. The sub-volume may be less than ½, less than ⅓, less than ¼, or have another size ratio relative to the volume.

The sub-volume is positioned around the anatomy as an initial assignment. Since the transducer and/or the anatomy of interest may move relative to the patient, the sub-volume may be sized to cover any movement and/or may be altered in position (see act 40) to account for motion. To optimize frame rate and/or image quality enhancement for the sub-volume, the size is smaller than to account for likely movement. After the initial assignment, other assignments may occur to reposition the sub-volume.

In act 36, the volume of the patient is scanned with different values for scan settings for the sub-volume of the volume than for other parts of the volume. An ultrasound imaging system scans the volume. A separate scan is performed by the ultrasound imaging system for the sub-volume. The volume scan is for the entire volume including portions or all of the sub-volume. While the volume may be scanned with a lesser sample and/or scan line density, the volume scan may result in voxels representing the same parts of the patient as sub-volume voxels. Alternatively, the volume scan is just for parts of the volume not included in the sub-volume.

The values for the parameters for scanning the entire volume or full field of view are the same as for performing the initial scan of act 30. The ultrasound imaging system continues to image the full field of view. The scanning of the full field of view may allow for viewing the orientation of a surgical device relative to the targeted anatomy or viewing of the anatomy of interest in the context of surrounding anatomy. The other parts of the volume outside of the sub-volume continue to be scanned.

Data from the volume scan overlapping with the sub-volume may be used as part of the sub-volume or only data from a separate sub-volume scan is used. One or more transmissions and resulting receive data are used just for the sub-volume.

Separate scans are performed for the sub-volume and volume. Different transmission and responsive receive events occur for the sub-volume scan than for the volume scan. The volume is scanned with scan settings having the different values than for the sub-volume. Any one or more (e.g., two or more) parameters have different values. For example, the line density, transmit power, frame-rate, line (scan) orientation, scan format, axial response (e.g., a different pulse shape or introduce harmonic imaging within the sub-volume) and/or transmit focus are different for the sub-volume scan than for the volume scan. In one embodiment, the sub-volume is scanned with a greater frame rate, resolution, contrast, or combinations thereof as compared to the larger volume. For example, the line density is greater for the sub-volume than for the volume.

In the valve example, the scan settings for the sub-volume scan are optimized for valve imaging, such as having a greater frame rate than the volume. The frame rate may be more important than resolution or contrast, so may be set higher with a sacrifice in resolution and/or contrast. The resolution and/or contrast for the sub-volume may be the same, better, or worse than for the volume. The focus points may be centered in the sub-volume for better focus as compared to using the volume scan. The transmit energy for the sub-volume may be higher than for the volume. The values are set for the anatomy of interest, so may be set relative to each other for the sub-volume and relative to the volume. Scanning other anatomy may use the same or different tradeoffs.

Figure 2:
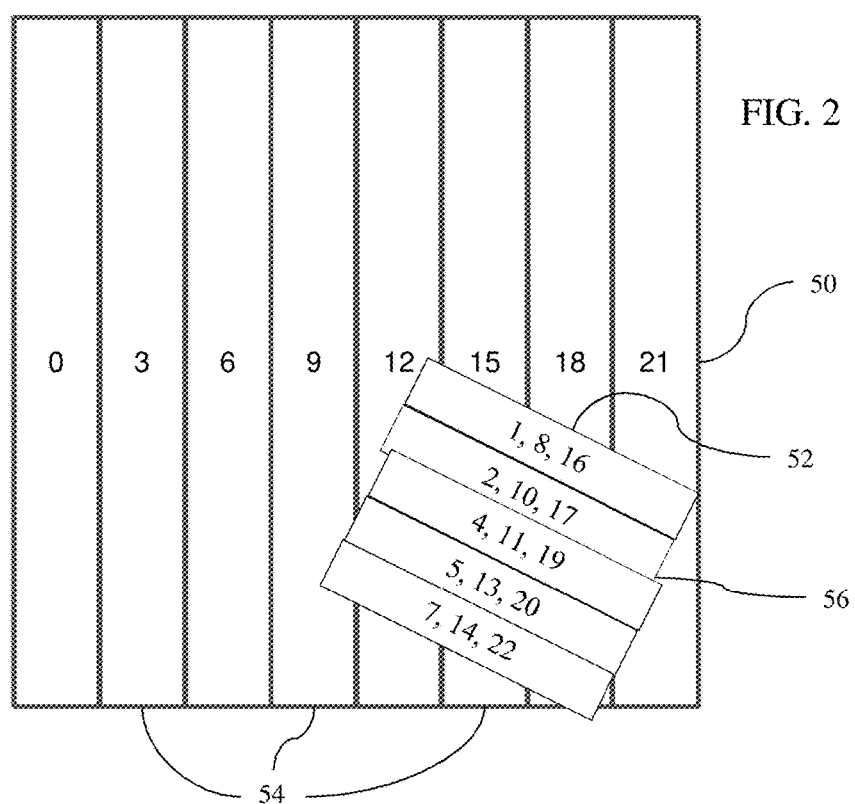
FIG. 2 illustrates one embodiment of interleaved scanning of a volume and sub-volume.

The orientation of the scan for the sub-volume may be the same or different than for the volume. FIG. 2 shows an example where the volume 50 is scanned along slices 54, and the sub-volume 52 is scanned along slices 56. The scan lines are along the slices 54, 56, such as scan lines being vertical for the slices 54 (i.e., orthogonal to the transducer array) and other than vertical for the slices 56. Any angular difference may be used, such as different by at least 10 degrees for comparing two linear scans. Where sector or vector scanning is provided, the difference is by at least 10 degrees from a center line or over half of the scan lines. By steering the scan lines differently, different aspects of the anatomy may be highlighted in the imaging. A valve may be best viewed from an angle of incident acoustic energy different than the angle of the energy to the heart. By using separate scans, the volume and sub-volumes may be scanned with appropriate settings for the anatomy. The main volume might be optionally reoriented either once or continuously on a slowly evolving basis to show a projection of the anatomical feature that is the standardized convention for certain exams or interventions.

The type of scan, such as the mode of scanning, is the same or different for the volume than the sub-volume. For example, harmonic imaging is used for the sub-volume but fundamental B-mode is used for the sub-volume. Non B-mode scanning (e.g., volume color Doppler, spectral Doppler, or elastography) of the sub-volume or other region of interest may also be oriented with the sub-volume.

The volume and sub-volume are scanned in an interleaved manner. The sub-volume is scanned once, twice, or more for every scan of the volume. By interleaving complete volume with complete sub-volume scans, a limited number of frame rate ratios are provided.

In another embodiment, the interleaving is of regions or sub-parts of the volume with the complete or sub-parts of the sub-volume. This interleaving may provide for a greater range or resolution in the frame rate ratio. Any region division of the volume and/or the sub-volume may be used. FIG. 2 shows an example with interleaving by slices. Each slice 54, 56 is a planar scan region. One or more planar scan regions of the volume 50 are scanned for each planar scan region of the sub-volume 52, or vice versa. Scanning of any number of slices 54 of the volume 50 may be interleaved with scanning any number of the slices 56 of the sub-volume 52. Scanning of the sub-volume 52 is interleaved with scanning of the larger volume 50.

Scanning is interleaved between sweeps (i.e., one or more slices 54, 56). A sweep is a collection of temporally consecutive transmit/receive events that progress in the same plane or planes. An imaging volume 50, 52 is generally constructed from multiple sweeps of scanning. This granularity is maintained in scan interleaving to improve lateral coherent processing between beams that are collected consecutively. N sweeps of the sub-volume are scanned for each M sweeps of the main volume, where N and M are integers≥1. In FIG. 2, the volume 50 is divided into eight slices 54. The sub-volume 52 is divided into five slices 56. This yields an effective ratio of (N*NumMainvolumeSweeps)/(M*NumSubvolumeSweeps) (e.g., N*8/M*5) between the sub-volume frame-rate and the main-volume frame rate.

Each sweep of the volume slices 54 requires a given time, such as 8 mS. Without sub-volume acquisition, this has a period of 64 mS, (15.525 Hz). After identifying a feature of interest, the sub-volume is acquired in 5 azimuthal sweeps with higher beam density and independent orientation, for example, resulting in each sweep of the sub-volume requiring 2 mS. Other timing may be provided.

In FIG. 2, the numbers indicate interleaved acquisition order of sweeps between the main volume and the sub-volume. For example, the slices 54 labeled with numbers 0 and 3 are separated by scans of two of the slices in the sub-volume. The sub-volume slices may be labeled as (top to bottom): 1, 8, 16, . . . ; 2, 10, 17, . . . ; 4, 11, 19, . . . ; 5, 13, 20, . . . ; and 7, 14, 22, . . . . The label numbers indicate the sequence of scanning by sweep or slice consecutively 1-22.

An identical frame-rate may be achieved between the sub-volume and the main volume by choosing N and M so that the ratio N/M=NumSubvolumeSweeps/NumMainvolumeSweeps. To increase frame-rate for the sub-volume, two or more sweeps of the sub-volume 52 for each sweep of main sub-volume 50 are performed. For example, the sub-volume period of 5*2+2.5*8=30 mS, (33.33 Hz), and the main-volume period of 8*(4+8)=96 mS (10.42 Hz). A 33% reduction in main volume frame rate is traded for 113% relative increase of sub-volume frame rate and increased resolution. Other possible sub-volume to main-volume rate relationships include: 1.0, 1.6, 2.0, 2.4, 3.0, 3.2, 4.0, . . . in the example of FIG. 2.

In one approach, the processor finds a minimum product M*N, with M>N, such that minimum target frame rate of sub-volume is achieved. Presets or other selection approaches may be used. The target frame rate is provided, such as based on the anatomy of interest. Other scan parameters are set given this starting criteria.

The proposed interleaving also works for two-dimensional imaging, with a two-dimensional frame being viewed as a degenerate version of volume imaging where the frames comprise only a single sweep. In this case, any increase in the sub-ROI frame rate relative to the main ROI is in terms of integer multiples.

Referring again to FIG. 1, in act 38, the data representing the sub-volume is combined with the data representing the volume. The samples acquired by separate scanning of the sub-volume and volume are combined by a filter or processor. Where the volume scan is of parts other than the sub-volume, the combination provides a data set representing the entire volume without overlap. Where the volume scan includes the sub-volume, the data for the overlap is averaged, a maximum selected, a minimum selected, or otherwise combined for any locations represented in both data sets. The resulting data after combination represents the volume, but with enhanced information in the sub-volume.

The data for the volume may be acquired at a different spatial resolution and/or temporal resolution than for the sub-volume. For example, the sub-volume data represents the sub-volume at 1.5 times the spatial resolution (e.g., 1.5 line and sample density) and twice the frame rate. To avoid or limit artifacts in imaging or data used for measuring, a spatial and/or temporal blending scheme harmonizes frame-rate, geometry, and display differences between the sub-volume and the larger main volume.

Temporal interpolation may be used. The lower frame rate data sets are temporally interpolated to create intervening data sets to provide a frame rate equal to the higher frame rate. For example, the frame rate of the volume is doubled by interpolating a frame of data temporally in-between each adjacent pairs of data sets. The interpolation is between data for the same location from different times. The interpolation provides blended frames at the frame rate of the sub-volume, which is greater than or equal to that of the main volume.

In one embodiment, $m_k$ is a vector of sample intensities corresponding to each main volume frame k after detection and before or after scan conversion. $s_l$ is a vector of sample intensities corresponding to each sub-volume after frame I after detection and before or after scan conversion. $t_k$ is the time that acquisition of each main volume frame k completes. $t_l$ is the time that acquisition of each sub-volume frame k completes. For each sub-volume $s_l$, a blended output frame of samples is computed as: $o_l = W[\alpha m_n - \beta m_{n-1}] + s_l$ where frames n and n−1 are the most temporally proximate main volume frames acquired at times $t_n \geq t_l > t_{n-1}$, and with $\alpha = (t_n - t_l)/T_m$ where $T_m$ is the main volume frame period and $\beta = 1 - \alpha$, and W[ ] is a masking function setting all main volume samples falling within the bounds of the sub-volume to zero. Thus, the output frame rate is equal to the sub-volume frame rate, with output frame samples outside the sub-volume being linearly interpolated between the main volume frames immediately preceding and following the sub-volume frame, and with samples falling within the sub-volume taken unmodified from the sub-volume. Other approaches may be used, such as employing motion compensation.

Alternatively or additionally, the data is combined to have a same effective spatial resolution. For example, the sub-volume has a greater sample and/or line density. The data of the volume is interpolated spatially to have a matching sample and/or line density. Spatial interpolation of data from the same time is used. The blended frames have a dense acoustic grid that matches the resolution of the sub-volume.

For combining, voxels from the volume data may overlap with voxels from the sub-volume data. Spatial blending is used to limit or avoid boundary artifacts of the sub-volume boundary with the volume. The blending provides a more gradual transition from the higher spatial resolution and/or contrast of the sub-volume with the volume, avoiding a distracting image artifact from a sudden transition.

Figure 3:
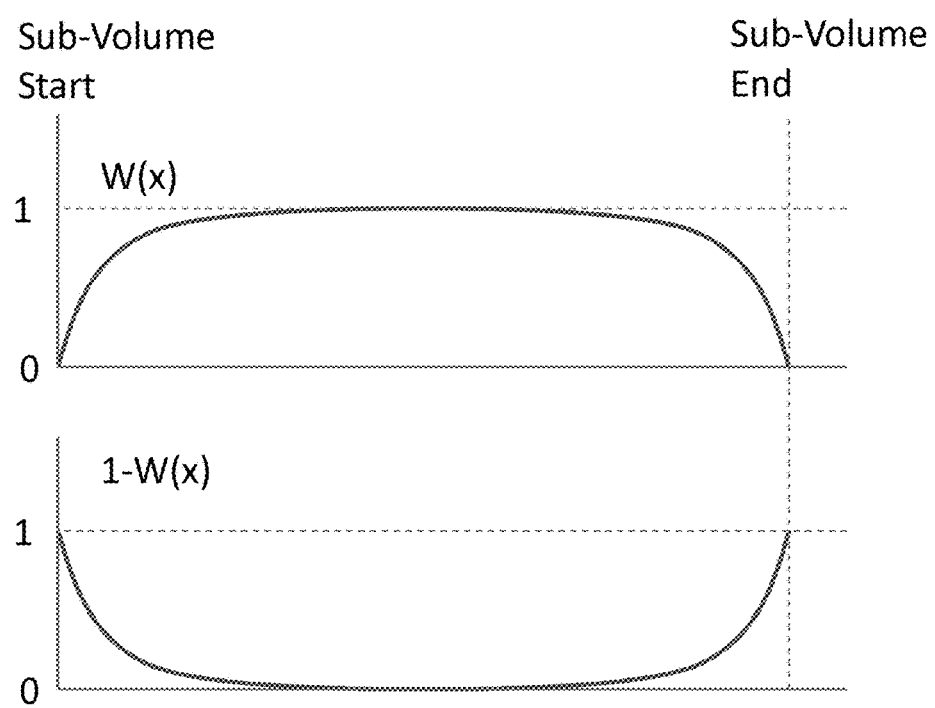
FIG. 3 illustrates example weighting for blending sub-volume data with volume data.

A boundary region of overlapping voxels in the sub-volume is defined. Within this boundary region a weighted combination is performed. Near the volume, the data or voxels from the volume are more heavily weighted in a weighted average. For locations more in the sub-volume, the data or voxels from the sub-volume are more heavily weighted in the weighted average. Any mapping function transitioning weights may be used. FIG. 3 shows a smooth weighting scheme such that the borders of the sub-volume are not obvious. In FIG. 3, the weight applied to the sub-volume data is W(x) and the weight applied to the volume data is 1−W(x). For locations of the volume outside the sub-volume, the weight applied to the volume data is 1. The weighting profile applied to the sub-volume data within the sub-volume along a dimension is an inverse of the profile applied to main volume data within sub-volume along the dimension. The same or different weighting profiles are applied across other dimensions.

Other weighting profiles may be used. In one embodiment, a spherical symmetry weighting is used. The distance from a center of the sub-volume indicates the relative weight. For voxel locations spaced further from the center, the volume data is more heavily weighted.

Referring again to FIG. 1, the data from the volume and sub-volume scans is shown following two paths. One path includes acts 38 and 40 for tracking the anatomy position. For example, a data stream forwarded to CINE or measurement process includes the volume and sub-volume data already blended. The sub-volume acquisition is transparent to existing measurement or other applications, including the detection of the anatomy in act 32. Another path blends or combines the data after CINE, allowing imaging of the volume with visual enhancements to the sub-volume. Different rendering, transfer functions, shading, or other imaging process is applied to the sub-volume than to the volume. For this separate processing, the data from the volume and sub-volume is passed separately for post-CINE or rendering blending.

Figure 4:
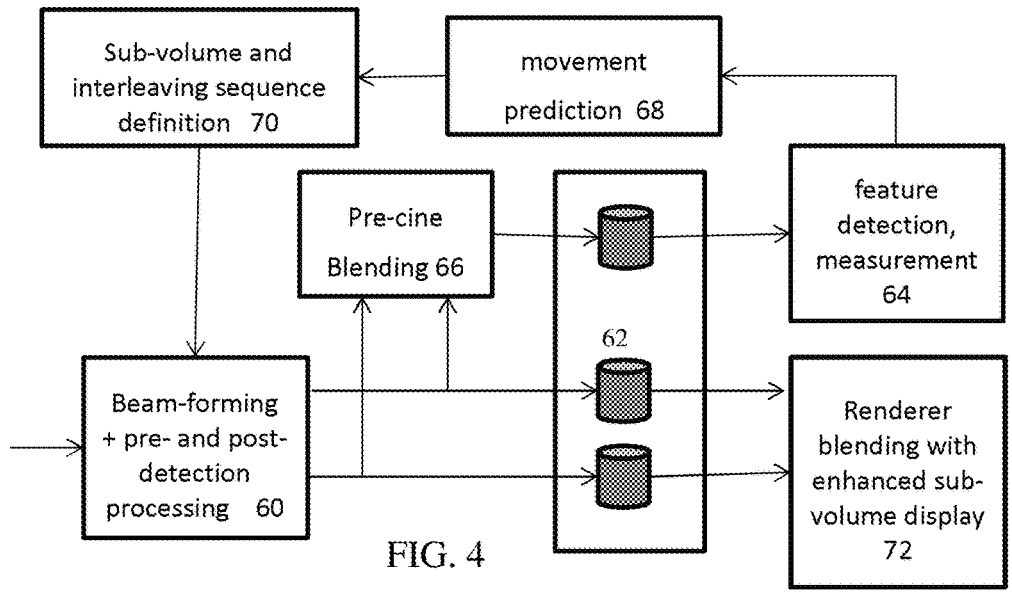
FIG. 4 shows one embodiment of different paths and uses for data from a volume and sub-volume.

FIG. 4 shows an example of this division. The beamforming and detection 60 are performed and data is passed in two paths to CINE 62—through a pre-CINE blending 66 and without pre-CINE blending. The blended data is used for feature detection and/or measurements 64 (e.g., existing volume, area, volume flow, or other diagnostic or process measurements). The measurements may be for setting the location of the sub-volume, so movement prediction 68 is used to define the sub-volume placement and resulting scan sequence 70. The un-combined data is provided to the renderer 72 for blending with enhanced or different rendering for the sub-volume and volume.

Referring again to FIG. 1, the blended data is used for measurement in act 40. The measurement is to track a position of the anatomy within the volume. The processor tracks using the data resulting from the scanning and as combined. For example, the processor performs the detection of act 32 to determine a current position of the anatomy. A classifier is applied to the combined data to detect the anatomy and the location of the anatomy. The detection is performed using the data set created by combining the sub-volume data with the volume data. In alternative embodiments, the tracking relies on similarity or correlation to determine a spatial offset and/or rotation. The anatomy is tracked by finding a position of the anatomy using data from a previous volume of data having a highest correlation in a current volume of data.

The tracking is performed without user input of an indication of the position of the anatomy. The processor performs the detection without user identification of a location of the anatomy. Alternatively, the user inputs an anatomy location.

By detecting a current position of the anatomy, the position and/or extent of the sub-volume are continuously redefined. The detection of the anatomy is as continuous as possible, with corresponding updates made periodically to the sub-volume scan-sequence. Continuous detection may be at least once every five seconds. More frequent detection, such as once for every volume data set, may be used. The beams of the sub-volume may be selected from a precomputed dense grid to minimize computation per update of the sub-volume.

The tracking indicates an alteration in the location of the anatomy and corresponding sub-volume. Based on the most recent detection of the anatomy, the sub-volume is positioned in act 34. Act 34 is repeated. The processor sets the location and/or extent of the sub-volume based on a most recent detection of the anatomy. As the anatomy moves relative to the volume, such as due to transducer and/or patient movement, the sub-volume location is updated to follow the anatomy in the volume field of view.

The alteration may be predictive. Since the motion may be continuous, the location of the anatomy may shift by the time the sub-volume is scanned. The delay from completing a scan in act 36 to starting the scan again in act 36 may result in the anatomy being at a different location from the detected location in the previous scan. This inaccuracy may be acceptable given a margin in the sub-volume. Alternatively, the processor predicts the next location. The motion from one or more previous pairs of acquired data sets is used to predict the next location for when the next scan is to occur. If the anatomy is moving at a given rate and direction, the rate and direction are used to predict the location by the time the next scan of the sub-volume is to occur. A history of motion, such as associated with cyclical motion, may be used in the prediction. The current phase is used to determine an expected rate and direction for the subsequent scan. The prediction compensates for the lag between feature detection and the real-time acquisition.

The feedback arrow from act 40 to act 32 represents on-going or continuous scanning. The scanning is repeated with the altered location of the sub-volume based on repeated detection of the anatomy. This process continues over time in the live or real-time imaging, tracking the anatomy in the volume. The anatomy of interest continues to benefit from greater frame rate, resolution, and/or contrast (i.e., image quality) over time despite movement. By tracking automatically, the sub-volume may be made smaller, allowing for more optimized imaging of the anatomy while providing the context from the larger volume.

In act 42, the data from the scanning of act 36 is used to generate an image. The processor, renderer, or other device generates an image from the volume and sub-volume data. For example, the data from the scanning of the volume and the data from the scanning of the sub-volume are passed to a three-dimensional renderer.

The data is passed as uncombined data. For example, the data is stored without blending in CINE memory or other memory. The renderer obtains the uncombined data and generates an image or images. In this path, separate image data streams for the volume and sub-volume are used for imaging. This allows display of an enhanced depiction of the sub-volume, such as with different textures, transparency, color mapping, shading, rendering, or other imaging. Other image processes, such as zooming to the sub-volume to image without the volume, may use the sub-volume data without any alteration due to blending. The smooth weighting from the combination may hide the sub-volume boundaries in the displayed image. Rather than alter the data, different rendering settings may be used to best display the sub-volume, such as with heightened resolution and contrast.

The sub-volume and volume may be rendered separately. Two different images are displayed adjacent to each other. In another embodiment, the sub-volume is rendered and a resulting image is overlaid on a rendering from the volume. The same viewing perspective, but different rendering (e.g., transfer function, type of rendering, color mapping, transparency, or shading) is used for both renderings. The anatomy may be specially marked in the display through luminosity, color, graphic frames, or other visible indicators.

In yet another embodiment, the sub-volume data is processed differently, such as by a different transfer function, but then combined with the volume data. The resulting blended data is rendered as an image. The combination is the same or different than in act 38. Samples from the sub-volume and the other parts are temporally and spatially blended so that the image represents the entire volume.

A sequence of images is generated. As the scanning is repeated, corresponding image generation is also repeated. Each newly acquired set of data representing the sub-volume and/or volume is used to generate an image. Live imaging updated as the data becomes available is performed. The images are generated at the same frame rate as the sub-volume and/or volume scan. For example, spatial and temporal blending is performed to provide images at the highest frame rate of the volume and sub-volume scanning. As another example, the portion of the image associated with the most recently acquired data is updated or replaced.

The images are B-mode images, but may be other modes. The image is generated without a graphic showing the sub-volume. The sub-volume is blended with the volume, but has a greater actual resolution, contrast, and/or frame rate. The volume has an interpolation created frame rate and/or resolution. Alternatively, a graphic or other difference indicates the sub-volume.

The imaging is used for diagnosis and/or treatment guidance. Enhanced imaging of valves may assist in interventional cardiology and structural heart diseases. The system continues to image the full field of view, which also assists in interventional applications where the orientation of a surgical device relative to the targeted anatomy is of prime interest. Enhanced imaging of other anatomy may be beneficial for other procedures.

In one embodiment, the imaging is minimally disruptive to existing user workflows. The user simply sees significantly improved image quality of the targeted anatomical feature without distraction or extra effort. The same values of the different settings other than the position of the sub-volume are used for a sequence of images showing the volume and the sub-volume. The value of the transmit focus, line direction, and/or aperture may or may not change based on any alteration of the sub-volume from one image to another.

If frame rates permit, more than one feature may be enhanced within the same large volume. The tracking is performed from different anatomy in the same volume. Different sub-volumes or a larger sub-volume covering both tracked anatomy are used.

The three-dimensional images are generated with rendering. Any rendering may be used, such as projection or surface rendering. Shading may or may not be added.

FIG. 5 shows one embodiment of a system 10 for enhanced ultrasound imaging of a sub-volume. The user configures the system 10 for volume or three-dimensional imaging, such as selecting an application for volume imaging specific anatomy. The user may alter values of one or more presets as desired. Once scanning starts, the system 10 automatically detects anatomy, scans the anatomy differently than the remaining volume in the field of view, and generates an image or images showing both the volume and sub-volume, but with enhanced imaging quality for the sub-volume. By tracking or detecting the anatomy in an on-going basis, the system 10 re-orients the sub-volume for enhanced imaging relative to the volume, providing volume imaging for a full field of view with better image quality for the anatomy of interest automatically. The frame rate for the sub-volume may be enhanced relative to the frame rate for the volume in a granular manner by interleaving by slices. Different data paths in the system 10 may be used for combined and uncombined volume and sub-volume data.

The system 10 is an ultrasound imager. In one embodiment, the ultrasound imager is a medical diagnostic ultrasound imaging system. In alternative embodiments, the ultrasound imager is a personal computer, workstation, PACS station, or other arrangement at a same location or distributed over a network for real-time or post acquisition imaging.

The system 10 implements the method of FIG. 1 or other methods. The system 10 includes a transmit beamformer 12, a transducer 14, a receive beamformer 16, an image processor 18, a blending processor 20, a renderer 21, a display 22, a beamformer controller 24, and a memory 26. Additional, different or fewer components may be provided. For example, the receive beamformer 16 through the display 22 represents a B-mode processing path of an ultrasound imager. Other components may be provided in the path, such as a spatial filter, a scan converter, a mapping processor for setting dynamic range, or an amplifier for application of gain. As another example, a user input is provided.

The transmit beamformer 12 is an ultrasound transmitter, memory, pulser, analog circuit, digital circuit, or combinations thereof. The transmit beamformer 12 is configured to generate waveforms for a plurality of channels with different or relative amplitudes, delays, and/or phasing to focus a resulting beam at one or more depths. The waveforms are generated and applied to a transducer array with any timing or pulse repetition frequency. For example, the transmit beamformer 12 generates a sequence of pulses for different laterally and/or range regions. The pulses have a center frequency.

The transmit beamformer 12 connects with the transducer 14, such as through a transmit/receive switch. Upon transmission of acoustic waves from the transducer 14 in response to the generated waves, one or more beams are formed during a given transmit event. The beams are for B-mode or other mode of imaging. Sector, Vector®, linear, or other scan formats may be used. The same region is scanned multiple times for generating a sequence of images. The formed beams have an aperture, origin on the transducer 14, and angle relative to the transducer 14. The beams in the field of view have a desired line density and format.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. For example, the transducer 14 is a one-dimensional PZT array with about 64-256 elements.

The transducer 14 connects with the transmit beamformer 12 for converting electrical waveforms into acoustic waveforms, and connects with the receive beamformer 16 for converting acoustic echoes into electrical signals. The transducer 14 transmits the transmit beams where the waveforms have a frequency and are focused at a tissue region or location of interest in the patient. The acoustic waveforms are generated in response to applying the electrical waveforms to the transducer elements. The transducer 14 transmits acoustic energy and receives echoes. The receive signals are generated in response to ultrasound energy (echoes) impinging on the elements of the transducer 14.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission for detection. Dynamic focusing on receive may be provided. The receive beamformer 16 outputs data representing spatial locations using the received acoustic signals. Relative delays and/or phasing and summation of signals from different elements provide beamformation. In alternative embodiments, the receive beamformer 16 is a processor for generating samples using Fourier or other transforms. The sampling density by the receive beamformer 16 is for a range of depths. Timing is used to select the range of depths over which the sampling occurs. The receive beams have a desired scan line density at an orientation or orientations using an aperture.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental, or other band. The fundamental frequency band may alternatively be used.

The receive beamformer 16 outputs beam summed data representing spatial locations. Data for locations for a volume and/or sub-volume are output.

The beamformer controller 24 and/or another processor configure the beamformers 12, 16. The beamformer controller 24 is a processor, application specific integrated circuit, field programmable gate array, digital circuit, analogy circuit, combinations thereof, or other device for configuring the transmit and receive beamformers 12, 16.

The beamformer controller 24 may use the memory 26 to acquire and/or buffer values for different beamformer parameters. The values may be accessed by the beamformers 12, 16 and/or loaded from the memory 26 into buffers of the beamformers 12, 16 to configure the beamformers 12, 16. By loading values into registers or a table used for operation, the values of acquisition parameters used by the beamformers 12, 16 for three-dimensional imaging are set. Any control structure or format may be used to establish the imaging sequence. The beamformers 12, 16 are caused to acquire data for three-dimensional imaging at a frame rate, with a transmit focus, at an imaging frequency band, over a depth, with a line density, at a sample density, and/or line orientation. Different values of one or more acquisition or scanning parameters may result in a different frame rate, signal-to-noise ratio, penetration, contrast and/or resolution.

The beamformer controller 24 causes the beamformers 12, 16 to scan a volume of a patient. Any three-dimensional scan format may be used. Similarly, the beamformer controller 24 causes the beamformers 12, 16 to scan a sub-volume of the volume. Any three-dimensional scan format may be used to scan the sub-volume.

The sub-volume scan is separate from and/or acquires additional data not acquired for the rest of the volume. For example, the sub-volume is scanned with scan lines at a different angle or angles than the rest of the volume. The angle relative to the tissue and/or the transducer is different. The volume and sub-volume are scanned at different orientations. Other parameters may be set to scan the sub-volume at a greater resolution, contrast, and/or frame rate as compared to the rest of the volume.

The beamformer controller 24 configures the beamformers 12, 16 to interleave scanning of the volume with the sub-volume. The scanning may be interleaved by complete volume/sub-volume scans or by parts. In one embodiment for interleaving by parts, the scanned volume includes a plurality of volume regions sequentially scanned during the scan of the volume. The volume regions may be planar slices, but other scan line groupings may be used. The volume is divided into different regions for sequential scanning, such as scanning different planes sequentially. The scanned sub-volume also includes a plurality of sub-volume regions sequentially scanned during the scan of the sub-volume. The sub-volume regions may be planar slices, but other scan line groupings may be used. The sub-volume is divided into different regions for sequential scanning, such as scanning different planes sequentially. The scan of the volume regions is interleaved with the scan of the sub-volume regions so that at least one of the volume regions is scanned before scanning all of the sub-volume regions and at least one of the sub-volume regions is scanned before scanning all of the volume regions. For example, the scan of N of the sub-volume regions is interleaved with each scan of M of the volume regions where N and M are integers greater than or equal to one. The beamformer controller 24 is configured to set the relative frame rates, such as finding a minimum product of N*M with M>N where a target frame rate occurs.

The image processor 18 detects, such as detecting intensity, from the beamformed samples. Any detection may be used, such as B-mode and/or color flow detection. In one embodiment, a B-mode detector is a general processor, application specific integrated circuit, or field programmable gate array. Log compression may be provided by the B-mode detector so that the dynamic range of the B-mode data corresponds to the dynamic range of the display. The image processor 18 may or may not include a scan converter.

In one data path for the volume and sub-volume data output by the image processor 18, the volume and sub-volume data are output separately or as different data sets to the renderer 21. The renderer 21 is a graphics processing unit, graphics card, separate computer, processor, or other device for three-dimensional rendering. The renderer 21 is configured by software, hardware, and/or firmware to generate an image or images of the patient from the volume and sub-volume data. Separate images for the volume and sub-volume may be generated. Alternatively or additionally, an image is generated to represent both the volume and the sub-volume in a single representation. The volume and sub-volume data may be separately processed (e.g., mapped to color or intensity) and then combined for rendering. Alternatively, the volume and sub-volume data are separately rendered and then the resulting rendered data is combined into the image. A sequence of such images may be generated.

The display 20 is a CRT, LCD, monitor, plasma, projector, printer or other device for displaying an image or sequence of images. Any now known or later developed display 20 may be used. The display 20 displays three-dimensional representations. The display 20 displays one or more images representing the volume and the sub-volume.

The spatial resolution and/or image quality is based, in part, on the acquisition or scan parameters. The ultrasound imager using different acquisition parameters may result in different spatial resolutions, temporal resolution, or image quality for the displayed image. The sub-volume part of the images has a greater image quality than the volume part, but the volume part is still provided for context. The sub-volume may shift in location due to tracking, allowing the user to continue to view the anatomy of interest with higher quality compared to the rest of the volume in a seamless way not requiring user input.

The blending processor 20 is a general processor, controller, digital signal processor, application specific integrated circuit, field programmable gate array, graphics processing unit, digital circuit, analog circuit, combinations thereof, or other device for processing data. The blending processor 20 is configured by hardware, software, and/or firmware to blend the data from the scan of the sub-volume with the data from the scan of the volume. Rather than just using the volume scan data, the sub-volume data may be blended with the volume data to provide a representation of the volume with greater quality for the sub-volume.

The blending processor 20 is configured to combine the data from the volume and sub-volumes. Spatial, temporal, or spatial and temporal harmonization may be applied. Any weighting may be used for blending. The blending is the same or different than used for imaging. In alternative or additional embodiments, the blending processor 20 outputs combined data to the renderer 21 for rendering.

One or more processes implemented by the system 10 may expect or be designed to operate on data representing the full volume. The process may perform better with the blended information. For example, the blended data is used for quantification. To the extent that the measure uses information from the sub-volume, the measure may be more accurate due to increased temporal or spatial resolution. To the extent the measure also includes information from the volume, the combination allows for such measures. The volume and sub-volume data may be treated differently for quantification than for the imaging.

In one embodiment, the blended data is used for detecting anatomy. The sub-volume information may allow for more reliable detection due to increased quality. The volume information may allow for detection where the anatomy moves partially or entirely out of the sub-volume. Having combined data may provide for more accurate or consistent detection of the anatomy.

The blending processor 20, beamformer controller 24, image processor 18, renderer 21, or other processor is configured to detect the anatomy. A classifier is applied to the blended data to detect the position of anatomy in the volume. The detection is repeated over time to track the position of the anatomy at different times. The position of the anatomy at a future time may be predicted from past detection and/or modeling of motion of the anatomy. The beamformer controller 24 is configured to cause the transmit and receive beamformers 12, 16 to track a location of the anatomy over time of the sub-volume within the volume based on a position over time the detected anatomy.

The beamformer controller 24, image processor 18, blending processor 20, renderer 21, and/or the ultrasound imager operate pursuant to instructions stored in the memory 26 or another memory. The instructions configure the system for performance of the acts of FIG. 1. The instructions configure for operation by being loaded into a controller, by causing loading of a table of values (e.g., elasticity imaging sequence), and/or by being executed. The memory 26 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for enhanced ultrasound imaging of a sub-volume, the system comprising:
    a transmit beamformer;
    a receive beamformer;
    a transducer connectable with the transmit beamformer and the receive beamformer;
    a beamformer controller configured to cause the transmit beamformer and the receive beamformer to:
        scan a volume of a patient, the volume including a plurality of volume regions sequentially scanned during the scan of the volume;
        scan a sub-volume of the volume, the sub-volume including a plurality of sub-volume regions sequentially scanned during the scan of the subvolume;
        interleave the scan of the volume regions with the scan of the sub-volume regions so that at least one of the volume regions is scanned before scanning all of the sub-volume regions and at least one of the sub-volume regions is scanned before scanning all of the volume regions, the subvolume regions being less than the entire sub-volume and the volume regions being less than the entire volume, wherein the interleave comprises scan of N of the sub-volume regions for each scan of M of the volume regions where N and M are integers and N is greater than or equal to one;
        wherein the beamformer controller is configured to select the N and the M based on a minimum product of N*M with M>N where a target frame rate of the scan of the volume and/or the scan of the sub-volume occurs;
    a renderer configured to generate an image of the patient using data from the scan of the volume and data from the scan of the sub-volume; and
    a display configured to display the image.

2. The system of claim 1 wherein the beamformer controller is configured to cause the transmit beamformer and the receive beamformer to scan the volume at a first orientation and scan the sub-volume at a second orientation different than the first orientation.

3. The system of claim 2 wherein the first orientation is of scan lines relative to the patient and the second orientation is of scan lines relative to the patient, the first orientation different by at least 10 degrees for over half of the scan lines than the second orientation.

4. The system of claim 1 wherein the scan of the sub-volume has a greater resolution, contrast, or resolution and contrast than the scan of the volume.

5. The system of claim 1 further comprising:
    a processor configured to detect anatomy over time from the data from the scans of the volume and sub-volume;
    wherein the beamformer controller is configured to cause the transmit beamformer and the receive beamformer to track a location over time of the sub-volume within the volume based on a position over time of the detected anatomy.

6. The system of claim 5 wherein the beamformer controller is configured to cause the transmit beamformer and the receive beamformer to track the location without user input of an indication of the position of the anatomy.

7. The system of claim 5 wherein the beamformer controller is configured to cause the transmit beamformer and the receive beamformer to track the location with a prediction of the location at a future time.

8. The system of claim 1 further comprising:
    a processor configured to blend the data from the scan of the sub-volume with the data from the scan of the volume differently for quantification than for the image.

9. The system of claim 1 wherein the beamformer controller is configured to cause the transmit beamformer and the receive beamformer to perform the scan of the volume with a first line density and perform the scan of the sub-volume with a second line density greater than the first line density.

10. The system of claim 1 wherein the beamformer controller is configured to cause the transmit beamformer and the receive beamformer to perform the scan of the volume with the scan settings having different settings for two or more of line density, transmit power, frame-rate, focus depth, line orientation, frequency, axial response, or transmit focus than the scan of the sub-volume.

11. The system of claim 1 wherein the volume regions comprise planar slices and wherein the sub-volume regions comprise planar slices.

\* \* \* \* \*